United States Patent
Hoshino et al.

(10) Patent No.: US 8,855,743 B2
(45) Date of Patent: Oct. 7, 2014

(54) NON-CONTRAST MAGNETIC RESONANCE PERFUSION IMAGING

(75) Inventors: Tsutomu Hoshino, Palm Harbor, FL (US); Mitsue Miyazaki, Mount Prospect, IL (US)

(73) Assignees: Kabushiki Kaisha Toshiba, Minato-Ku, Tokyo (JP); Toshiba Medical Systems Corporation, Otawara-Shi, Tochigi-Ken (JP)

(*) Notice: Subject to any disclaimer, the term of this patent is extended or adjusted under 35 U.S.C. 154(b) by 0 days.

(21) Appl. No.: 13/470,052

(22) Filed: May 11, 2012

(65) Prior Publication Data

US 2013/0303885 A1 Nov. 14, 2013

(51) Int. Cl.
A61B 5/05 (2006.01)

(52) U.S. Cl.
USPC ........... 600/419; 600/407; 600/410; 600/411; 600/413; 600/418; 600/420

(58) Field of Classification Search
USPC ......... 600/407, 410, 411, 412, 413, 414, 415, 600/416, 417, 418, 419, 420, 421, 422, 600/423; 324/300, 307, 308, 309, 310, 311, 324/312, 313, 314, 315, 318, 319, 320, 321, 324/322
See application file for complete search history.

(56) References Cited

U.S. PATENT DOCUMENTS

| | | | |
|---|---|---|---|
| 6,498,946 B1 * | 12/2002 | Foo et al. | 600/410 |
| 7,328,054 B2 * | 2/2008 | Jesmanowicz | 600/410 |
| 2011/0071382 A1 | 3/2011 | Miyazaki et al. | |
| 2011/0080170 A1 | 4/2011 | Miyazaki | |

FOREIGN PATENT DOCUMENTS

| | | |
|---|---|---|
| JP | 10-328158 | 12/1998 |
| JP | 2000-342555 | 12/2000 |
| JP | 2007-190114 | 8/2007 |
| JP | 2009-261421 | 11/2009 |
| JP | 2011-083592 | 4/2011 |
| WO | 00/65995 A1 | 11/2000 |

OTHER PUBLICATIONS

Zun, et al., "Assessment of Myocardial Blood Flow (MBF) in Humans Using Arterial Spin Labeling (ASL) Feasibility and Noise Analysis," *Magnetic Resonance in Medicine*, vol. 62, pp. 975-983 (2009).
International Search Report mailed Aug. 13, 2013 in PCT/JP2013/063214.
Mitsue Miyazaki et al., "Nonenhanced MR Angiography," Radiology, Jul. 2008, vol. 248, No. 1, pp. 20-43.
M. Katoh et al., "Flow Targeted Coronary MR Angiography: Comparison of Three Different Spin Labeling Techniques," Proc. Intl. Soc. Mag. Reson. Med. 13, May 2005, p. 709.
Y. Wang et al, "High Resolution 3D MR Angiography using Arterial Spin Labeling," Proc. Intl. Soc. Mag. Reson. Med. 17, Apr. 2009, p. 94.

* cited by examiner

*Primary Examiner* — Tse Chen
*Assistant Examiner* — Jason Ip
(74) *Attorney, Agent, or Firm* — Nixon & Vanderhye PC

(57) ABSTRACT

A magnetic resonance imaging (MRI) system acquires MRI data within one patient breath-hold sufficient to generate (a) at least one tag-off first type non-contrast cardiac perfusion image using a data acquisition sub-sequence including a non-selective IR (inversion recovery) pulse and (b) at least one tag-on second type non-contrast cardiac perfusion image using a data acquisition sub-sequence including a non-selective IR pulse and a spatially selective IR pulse. A set of registered tag-on and tag-off images are differentially combined to produce an accurate cardiac perfusion image.

22 Claims, 11 Drawing Sheets

Simplified bull's eye images of three types
 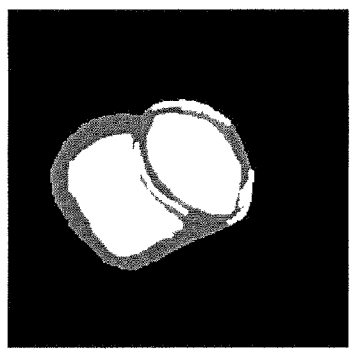 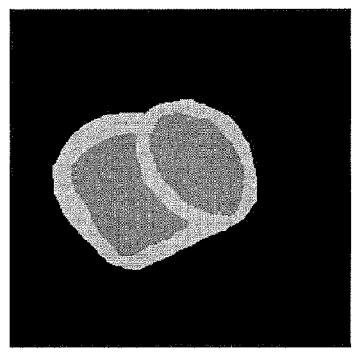
Fig. 6A (Type A)   Fig. 6B (Type B)   Fig. 6C (Type C)
Color blending of the processed image on a monochrome reference image.
Fig. 7
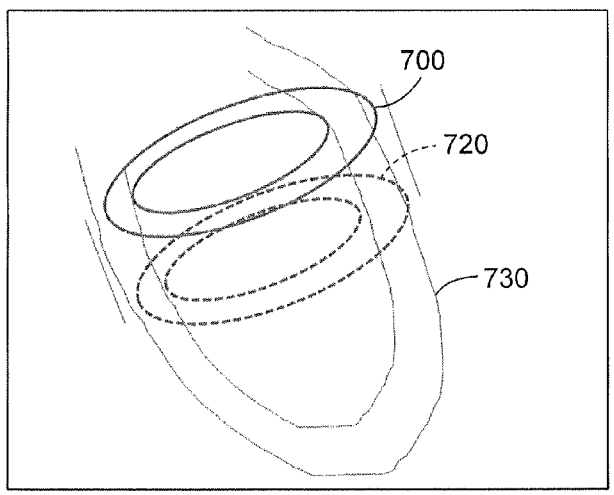
3D volume rendering of the processed slice images on 3D ventricle volume images.
Fig. 8

NON-CONTRAST MAGNETIC RESONANCE PERFUSION IMAGING

FIELD

The subject matter below relates generally to magnetic resonance imaging (MRI) apparatus and processes. In particular, the MRI processes described below involve enhancements to non-contrast tag-on/tag-off arterial spin labeling (ASL) MRI for imaging perfusion of flowing nuclei such as blood within patient tissue such as in myocardial perfusion imaging (MPI).

BRIEF DESCRIPTION OF THE DRAWINGS

FIGS. 6A, 6B and 6C are simplified exemplary "bull's eye" images of the three image types A, B and C, respectively corresponding to the sub-sequences of types A, B and C depicted at FIGS. 3-5;

FIG. 7 is an exemplary composite image wherein a processed image (based on differential combinations of image type A minus image type B) has been color blended onto a monochrome reference image for better visualization of the imaged perfusion patterns;

FIG. 8 is a schematic depiction of an exemplary 3D volume rendering of processed slice images onto a 3D ventricle volume image;

DETAILED DESCRIPTION

Figure 1:
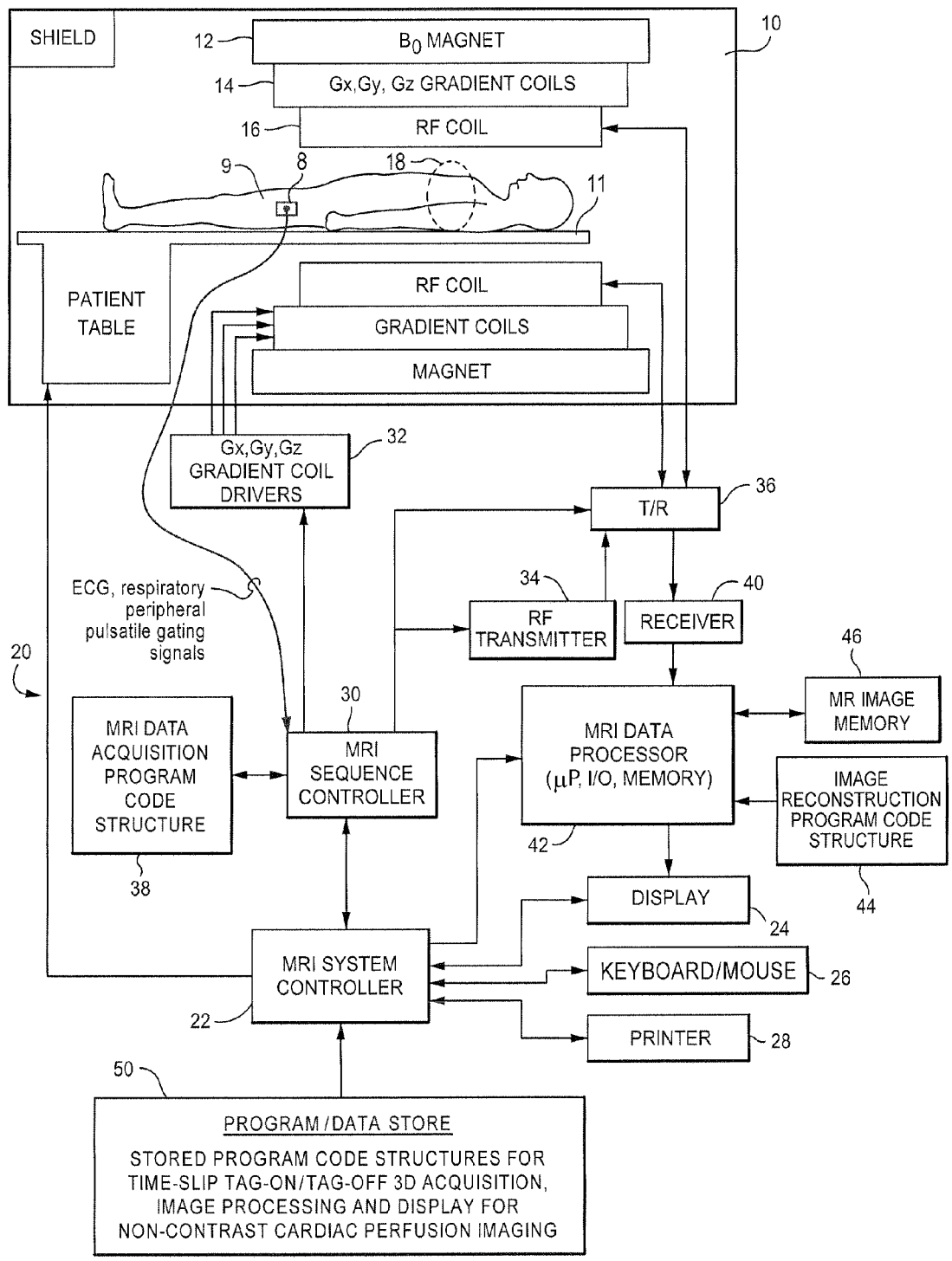
FIG. 1 is a high-level schematic block diagram of an exemplary MRI system embodiment adapted to acquire and process data for Time-SLIP (Spatial Labeling Inversion Pulse) MRI using tag-on/tag-off pulse patterns for 3D acquisition non-contrast MPI.

The MRI system shown in FIG. 1 includes a gantry 10 (shown in schematic cross-section) and various related system components 20 interfaced therewith. At least the gantry 10 is typically located in a shielded room. One MRI system geometry depicted in FIG. 1 includes a substantially coaxial cylindrical arrangement of the static field Bo magnet 12, a $G_x$, $G_y$ and $G_z$ gradient coil set 14 and an RF coil assembly 16. Along the horizontal axis of this cylindrical array of elements is an imaging volume 18 shown as substantially encompassing the heart tissue of a patient 9 supported by a patient bed or table 11.

An MRI system controller 22 has input/output ports connected to display 24, keyboard/mouse 26 and printer 28. As will be appreciated, the display 24 may be of the touch-screen variety so that it provides control inputs as well.

The MRI system controller 22 interfaces with MRI sequence controller 30 which, in turn, controls the $G_x$, $G_y$ and $G_z$ gradient coil drivers 32, as well as RF transmitter 34 and transmit/receive switch 36 (if the same RF coil is used for both transmission and reception). Additional body "surface" RF coils (perhaps in arrayed dispositions) may also be used for RF coupling to selected body tissues as will be understood. As those skilled in the art will appreciate, one or more suitable physiological transducers 8 may be affixed to the patient's body to provide ECG (electrocardiogram), respiratory and/or peripheral pulsatile gating signals to the MRI sequence controller 30. The MRI sequence controller 30 also has access to suitable program code structure 38 for implementing MRI data acquisition sequences already available in the repertoire of the MRI sequence controller 30—e.g., to generate non-contrast MRA (magnetic resonance angiography) and/or MRV (magnetic resonance venography) and/or blood perfusion tissue images using operator and/or system inputs defining particular MRI data acquisition sequence parameters.

The MRI system 20 includes an RF receiver 40 providing input to data processor 42 so as to create processed image data that may be sent to display 24. The MRI data processor 42 is also configured for access to image reconstruction program code structure 44 and to MR (magnetic resonance) image memory 46 (e.g., for storing MR image data derived from processing in accordance with the exemplary embodiments and the image reconstruction program code structure 44).

Also illustrated in FIG. 1 is a generalized depiction of an MRI system program/data store 50 where stored program code structures (e.g., for Time-SLIP tag-on/tag-off 3D acquisition, image processing and display of non-contrast cardiac perfusion imaging, operator inputs to same, etc.) are stored in computer readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those skilled in the art will appreciate, the FIG. 1 depiction is a very high-level simplified diagram of a typical MRI system with some modifications so as to practice exemplary embodiments to be described hereinbelow. The system components can be divided into different logical collections of "boxes" and typically comprise numerous digital signal processors (DSP), microprocessors, special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an MR imaging reconstruction process, an array of computer-readable accessible data value storage sites (e.g., multi-digit binary representations of pixel values) in physical storage media will be transformed from some prior state (e.g., all uniform "zero" values or all "one" values) to a new state wherein the physical states at the physical sites of such an array (e.g., of pixel values) vary between minimum and maximum values to represent real-world physical events and conditions (e.g., the tissues of a patient over an imaged volume space). As those in the art will appreciate, such arrays of stored data values represent and also constitute a physical structure—as does a particular structure of computer control program codes that, when sequentially loaded into instruction registers and executed by one or more CPUs of the MRI system 20, cause a particular sequence of operational states to occur and be transitioned through within the MRI system.

The exemplary embodiments described below provide improved ways to acquire and/or process MRI data acquisitions and/or to generate and display MR images.

Non-contrast MRA (magnetic resonance angiography) techniques make it possible to image blood perfusion in myocardium by using a non-spatially selective inversion pulse and a spatially selective inversion pulse to restore blood signals upstream of the imaged volume. However, using Time-SLIP 3D acquisition in accordance with previously known practices has encountered disadvantages such as the following:

In one teaching, 2D acquisition scans (i.e., where a slice is imaged using 2D Fourier Transformation based on acquired data that incorporates 2D phase encoding) has been used with no time adjustment of the flowing blood period. Not only was the observation area limited to a single slice due to a single 2D acquisition process; but, in addition, although blood travel time varies with each individual, only a single transit time (i.e., one BBTI (Black Blood Time to Inversion) was used.

In other approaches, two separate (i.e., over two respectively corresponding breath-hold periods) 2D or 3D acquisition scans (i.e., where data for a multi-slice volume is acquired in a single longer acquisition process incorporating 3D phase encoding) were used with the labeling on respectively corresponding acquisitions being tag-on and tag-off, causing misregistration and making it difficult to subtract the images without having significant registration errors.

The exemplary embodiment described below provides apparatus and methods to generate myocardium perfusion images from non-contrast cardiac images that are acquired using combinations of (a) a non-selective IR (Inversion Recovery) pulse and (b) a selective IR pulse—and to display the images in such a way that users can easily understand cardiac information on myocardium and blood perfusion through the coronary arteries, helping identify ischemic regions and/or infarction of myocardium.

Figure 2:
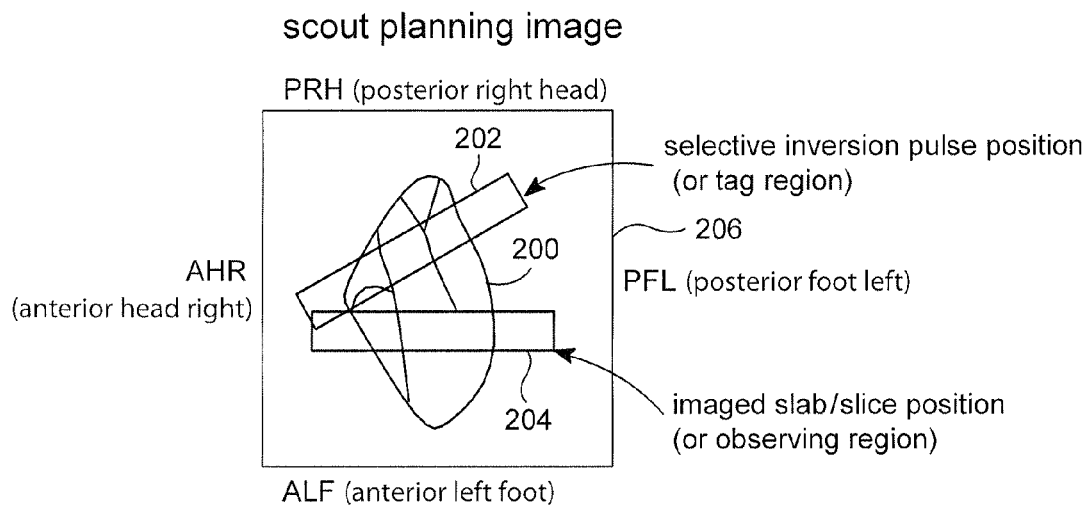
FIG. 2 is a schematic depiction of a scout/locator planning image for exemplary data acquisitions of type A, type B and type C in an exemplary embodiment.

A scout planning image is schematically depicted in FIG. 2. Here, A stands for anterior, P for posterior, H for head, F for foot, R for right and L for left. MRI images can be acquired with oblique angles, which means that one side of the images may correspond to Anterior, Head and Right-hand side at the same time, and are thus labeled as AHR. Of course, the other side of the image must be PFL in this case. A non-selective IR pulse is applied to the entire volume 206 and a spatially selective IF pulse is applied to an upstream volume 202 (e.g., above the cardiac tissue 200 of interest). 3D MRI data is then acquired for the imaged volume 204.

As will be explained in more detail below, multiple 3D MRI data sets are acquired in one breath-hold period to reduce misregistration during subsequent inter-image data processing.

A single breath-hold acquisition includes both 3D tag-off (non-selective IR pulse alone) and tag-on (both non-selective and selective IR pulses), where each slice or section encoding (actual imaging acquisition or read-out) is triggered at the same cardiac phase, preferably diastole. Repetitions of this process using different BBTIs (Black Blood Time to Inversion) can be implemented to observe the time course of marked (e.g., "tagged") blood travel into the myocardium.

In order to understand the period of blood travel time from the marked (tagged) region to the myocardium region of interest, a series of 2D acquisitions can be performed using different BBTIs triggered at the same cardiac phases in a breath-hold period or one 2D Time-SLIP acquisition with bSSFP (or FFE) segmented cine to provide a rough estimation of marked blood perfusion timing (meaning when blood supplies arrive to the myocardium).

Figure 3:
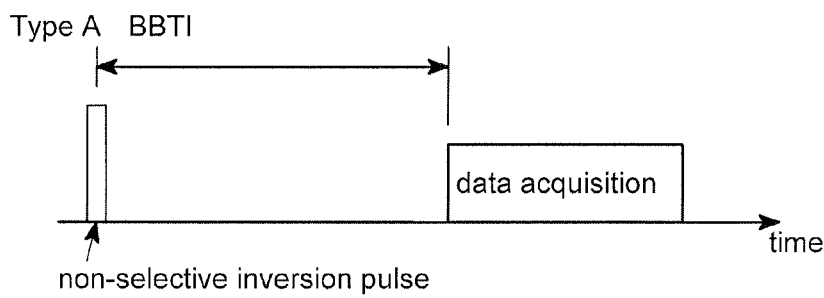
FIGS. 3-5 schematically illustrate in abbreviated fashion MRI data acquisition sub-sequences of the type A, type B and type C used in an exemplary embodiment.
Figure 4:
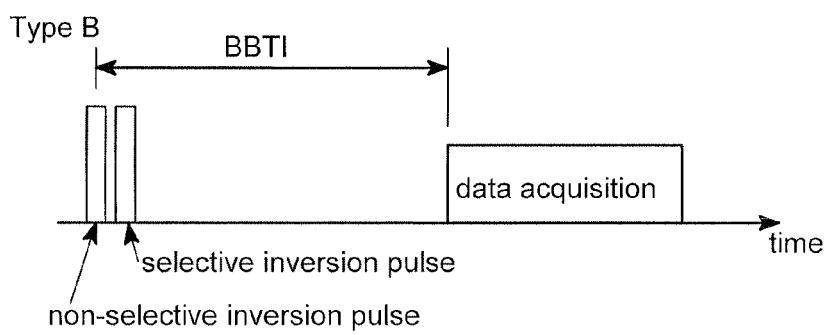

The non-selective IR pulse suppresses myocardium as well as blood flowing into the heart. If this pulse is used alone, both blood and myocardium will experience T1 recovery during imaging (FIG. 3, type A). If a selective IR pulse is also applied in an upstream region for the heart immediately after the non-selective IR pulse, then the blood signal is restored (i.e., tagged) before coming into the heart and the tagged blood will be imaged as bright pixels (FIG. 4, type B). A time constant, BBTI, controls the time in which the tagged blood is allowed to enter the heart, as well as how much T1 recovery the myocardium will have. By acquiring these two sets of images (one tag-on, one tag-off) within one breath-hold to minimize registration errors, blood contributions to the MRI signal can be isolated from myocardium by subtracting one image from the other (using complex-valued pixel-by-pixel image subtraction processes). To view lesions of ischemic myocardium or infarction where no (or little) blood flow is observed (as compared to normal myocardium), threshold and signal-reverse operations can be performed. Thus, the pixel value $I_i$ at pixel location i is calculated as:

$$I_i = (\theta_0 - \min(\theta_0, |A_i - B_1|)) F(\max(|A_i|, |B_i|), T_{BBTI}) \quad \text{[Equation 1]}$$

where $A_i$ and $B_i$ are complex numbers representing pixel values at pixel location i of a type A image and of a type B image, respectively, and $\theta_0$ is a threshold value. The subscript i in $I_i$ of Equation 1 is a shorthand notation for a pixel location (x,y) in an image. $\theta_0$ is a constant threshold value (over BBTI) that is to be adjusted based on the image for a given set of scan parameters. Once determined, it can be used for all patients. However, it is possible to let the user choose $\theta^0$ for each BBTI in order to change sensitivity to the difference between type A and type B depending on BBTI. In this case, $\theta_0$ is no longer a constant over BBTI. In order to prevent non-signal regions from being brightly imaged, a continuous threshold function of $|A_i|, |B_i|$, and BBTI is multiplied by function F. The dependency of BBTI is needed to compensate signal changes based on the T1 recovery of the tissue. An example of the function F is a sigmoid function like $$F(x, t) = \left( \frac{1}{1 + \exp\left(-\frac{x - g(t)}{6g(t)}\right)} \right) \quad \text{[Equation 2]}$$

where g(t) is a function that represents threshold changes depending on BBTI. An example of g(t) is one that takes into account the T1 recovery. F(x, t) is a sigmoid function whose value monolithically increases from 0 to 1. t determines where the value becomes 0.5. More precisely, when x=g(t), F(x, t) becomes 0.5. In this sense, g(t) is a threshold value and it changes depending on t. The function F masks out areas whose signal intensity is very small because:
1. the reverse intensity operation make areas bright where there are very small signal differences between A and B images;
2. this also includes areas where both signals of A and B images are very small from the beginning (e.g., air); and
3. F(x, t) makes these areas dark due to its smooth threshold operation.

$$g(t) = C \max\left(\epsilon, \left|1 - 2\exp\left(-\frac{t}{T_1}\right)\right|\right) \quad \text{[Equation 3]}$$

where C and $\epsilon$ are parameters to be adjusted and $T_1$ is the T1 recovery constant of myocardium, which is around 1,000 to 1,200 ms. C in the definition of g(t) in Equation 3 is a constant (over BBTI) and can be determined empirically. One way is to adjust C so as to make g(BBTI) equal the average myocardium signal in the region of interest. $\epsilon$ is simply a small number chosen so as to avoid possible attempted division by zero (for example, 0.01).

Figure 5:
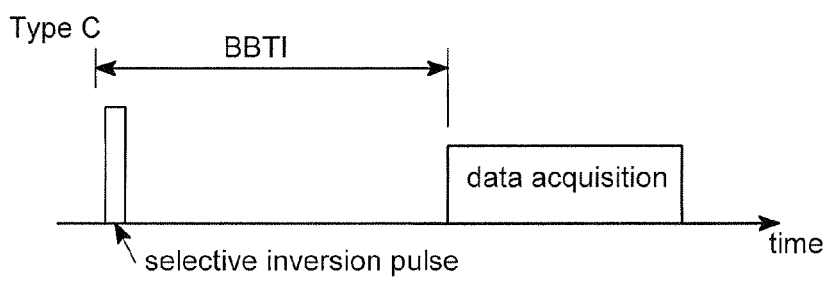

If only a selective IR pulse is applied in an upstream region for the heart, then the blood signal is reversed (tagged) by a 180° nutation before traveling downstream into the heart tissue and the tagged blood pixels will be imaged as being dark compared to the background (FIG. 5, type C). By acquiring these three sets of image types (A, B, and C) within one breath-hold to minimize registration errors, the myocardium can also be imaged by subtracting A from C because the signal from blood is the same for A and C, while the signal from myocardium is different between A and C. By applying a threshold operation, perfusion information in myocardium also can be extracted from the A and C image pair $$I_i = |A_i - B_i| F(|C_i - A_i|, T_{BBTI}) \quad \text{[Equation 4]}$$

in such a way that regions where blood flows into myocardium appear as being bright compared to the background.

The images created by Equation 1 normally do not image myocardium so brightly because the signal contribution from the myocardium is subtracted. This makes it difficult to see where the perfusion is taking place relative to myocardium tissue. To alleviate this situation, color image blending of a normal MRI image (of the same volume) registered with and blended with the A or B type images is performed showing the exact location of blood flow relative to myocardium. FIG. 7 is a sample image where an image created by Equation 1 is shown in cyan added onto a monochrome image of type A.

Multi-slice data acquisitions with various BBTI values allow generation of a 4D data set that shows perfusion dynamics as a function of time, with BBTI as a time-dimensional control variable. 3D volume rendering makes it easy to view how blood flows into myocardium via coronary arteries from any viewing angle. Cine viewing allows the user to see blood perfusion as a function of BBTI (time). FIG. 8 is a sample picture of 3D volume rendering of the processed slice images 700 . . . 720 on 3D ventricle volume image 730.

Acquiring data with a wide range of BBTI values, for example, 100 msec to 2,000 msec with a 200 msec interval, allows calculation of mean transit time between blood entering the coronary arteries and blood dissipating in the myocardium. Plotting signal intensity as a function of BBTI at some sampling points makes it possible to see variations of the mean transit time over locations.

By taking a minimum operation of all the images over BBTI, ischemic and/or infarct regions can be isolated as bright spots, which means that acquired signal did not change much between type A and type B over many BBTI values.

Type A and type B images are a minimum set of images that are preferably acquired within a single breath-hold in order to obtain a registered processed image that shows areas with no bright blood flow. All three type A, type B and type C images are preferably to be acquired within one breath-hold scan in order to get a different registered processed image (Equation 4) that shows bright blood flow areas. It is preferred to acquire all images within one breath-hold in order to avoid motion-related misregistration.

The preferred processing includes a combination of complex-valued subtraction, thresholding, reverse operation of image intensity and a masking operation by using the two types of images (A and B) or the three types of images (A, B and C).

The exemplary embodiment allows a single scan of both tag-on and tag-off 3D acquisitions to reduce misregistration. The image process provides easy observation of marked blood entering into the myocardium.

The cardiac information on myocardium and blood perfusion through the coronary arteries can be more easily visualized and understood because:
  there is less misregistration of the interleaved tag-on and tag-off images for subtraction;
  A versus B and/or A versus C image processing techniques provide clear depictions of perfusion;
  superimposition of a processed perfusion image with a different color scheme of an original cardiac image adds contextual clarity to the perfusion image;
  3D volume rendering of processed perfusion images also adds context to displayed perfusion images; and/or
  data plotting can show signal intensity versus BBTI at sampling locations to better visualize blood perfusion mean transmit time.

Figure 9:
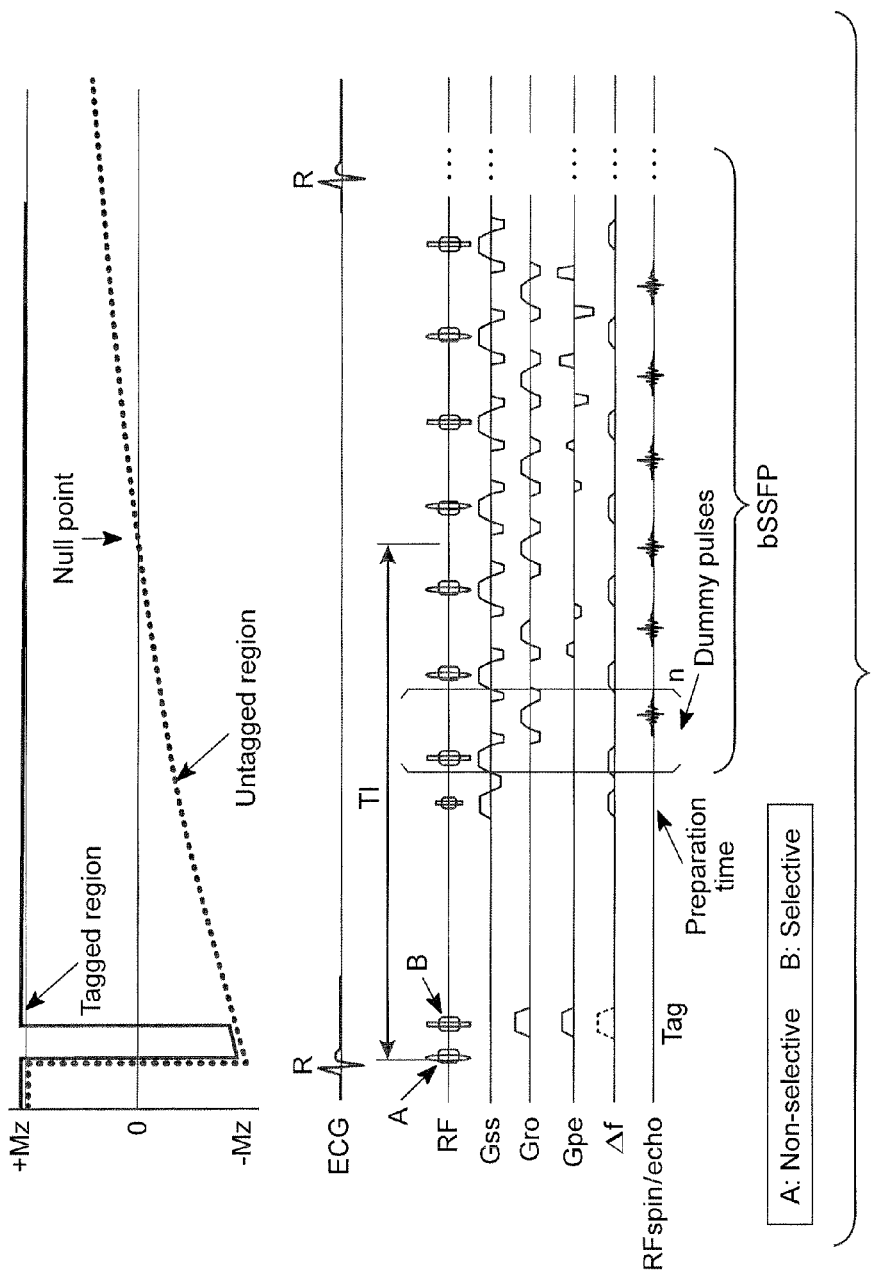
FIG. 9 is a schematic depiction of a 2D tag-on MRI data acquisition sequence using both non-selective and selective IR pulses during one breath-hold.

As depicted in FIG. 9, a 2D tag-on sequence can be used with both non-selective and selective inversion recovery (IR) RF pulses during one breath-hold. A preparatory breath-hold instruction is issued to the patient (e.g., by a pre-agreed upon audible sound issued to the patient within the gantry while in the imaging position). Of course, the respiratory function of the patient (e.g., physical changes in chest cavity dimensions) could also typically be monitored thereafter to ensure that the patient actually does engage in one sustained breath-hold throughout the required image data acquisition sequence.

As depicted in FIG. 9, when the non-spatially selective RF nutation pulse A occurs, it substantially reverses the Z-axis+ Mz magnetization of NMR nuclei to −Mz throughout the cardiac tissue of interest, including a blood input area that will become the tagged region. Thereafter, a spatially selective RF pulse B is imposed on the region to be tagged, thus again reversing its magnetization (i.e., back to +Mz) so as to now be realigned in the positive Z-axis direction where it substantially remains. However, the untagged region (including the region to be imaged) only decays exponentially (in accordance with its T1 value) towards realignment with the static magnetic field Bo in the positive Z-axis direction. At some point, it reaches a null point where there is effectively zero longitudinal magnetization in the untagged region (i.e., myocardium tissue to be imaged). While there is still a substantial difference in magnetization between blood that was in the tagged region (during the spatially selective RF pulse application B) and the cardiac myocardium (that was in the untagged region), imaging sub-sequences are effected for acquiring MRI data sufficient to generate at least one tag-on image of the myocardium tissue and at least one tag-off image of the myocardium tissue during one breath-hold. The exemplary MRI processes depicted in FIG. 9 for data acquisition include, for example, a conventional bSSFP (balanced steady-state free precession). As will be appreciated, other known MRI data acquisition sequences may be employed. As will be explained in more detail below, preferably sub-sequences for gathering tag-on and tag-off image data will be interleaved with respect to time during an overall image data acquisition sequence during one breath-hold.

Figure 10:
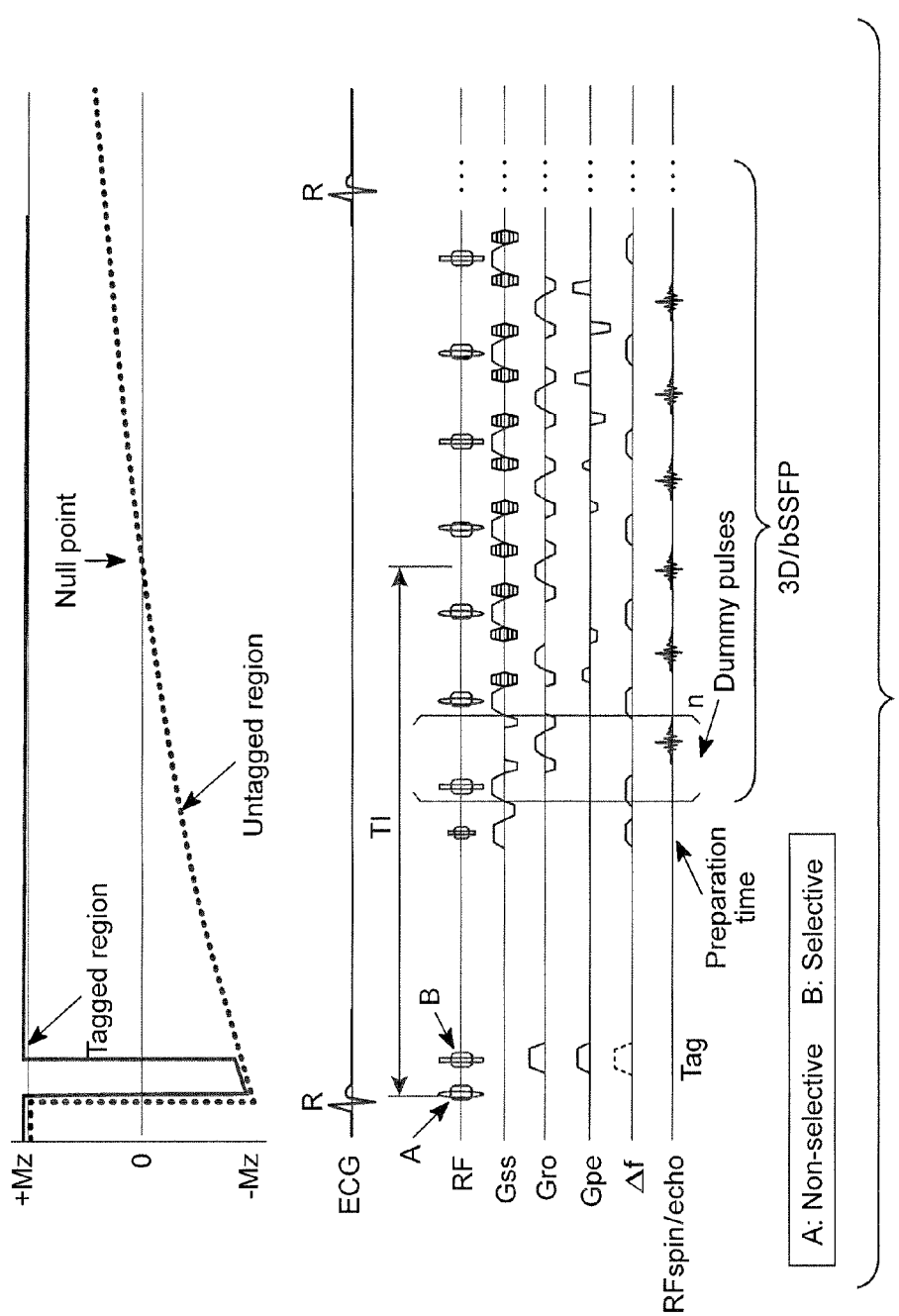
FIG. 10 is an exemplary schematic depiction of a 3D tag-on sequence using both non-selective and selective pulses during one breath-hold.

FIG. 10 is a similar depiction of a tag-on data image acquisition sub-sequence using both non-selective and selective IR RF pulses during one breath-hold—but now employing 3D phase encoding to acquire data for multiple slices constituting a desired volume of cardiac tissue. As those in the art will appreciate, a plurality of 2D slice images can be utilized to acquire data for a multi-slice region of tissue or, alternatively, a 3D acquisition sequence may be utilized with additional phase encoding orthogonal to the slices so as to acquire in one acquisition sequence sufficient phase encoded data to image an entire multi-slice volume if the captured data is subjected to appropriate 3D Fourier transformation.

Figure 11:
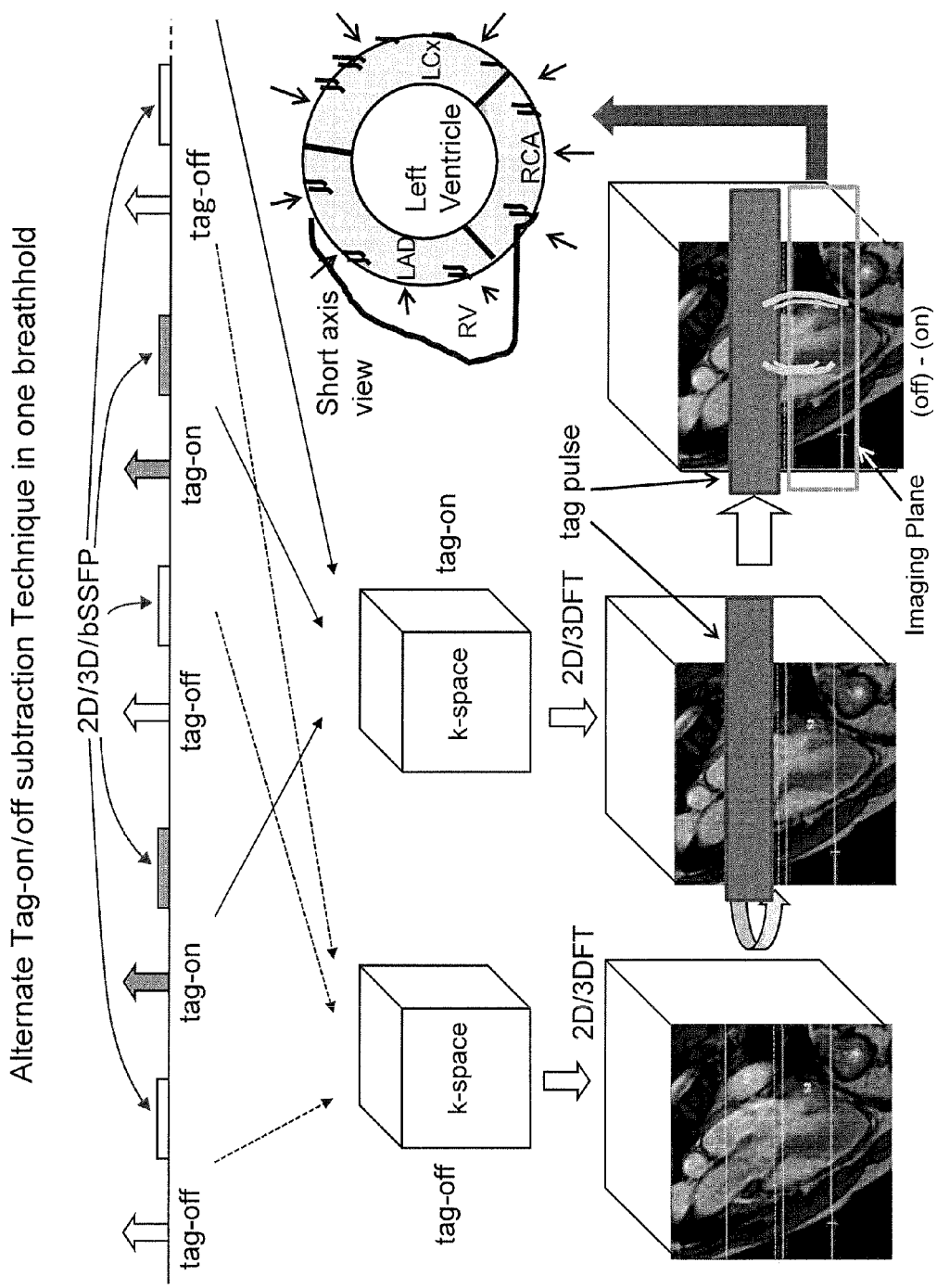
FIG. 11 is a schematic depiction of an alternating tag-on/tag-off interleaved MRI data acquisition sequence and resulting generated image subtraction techniques where the data is acquired in one breath-hold.

FIG. 11 schematically depicts the alternating, i.e., interleaved tag-on and tag-off data acquisition sub-sequences within one breath-hold—as well as image processing techniques. For example, a first tag-off excitation is followed by a first data acquisition sub-sequence (of either the 2D or 3D bSSFP type) so as to partially fill k-space with captured image data. Next, a tag-on excitation occurs, followed by a corresponding data acquisition sub-sequence that now captures image data to partially fill k-space for a tag-on image. This pattern alternates as required to completely fill k-space for tag-off and tag-on multi-slice images of a selected volume. Once all of the data has been acquired (e.g. by the interleaved sub-sequences acquiring partial tag-on and tag-off data through one breath-hold), differential processing, thresholding, and the like occurs so as to, in effect, subtract the tag-on image from the tag-off image on a pixel-by-pixel (using complex-valued arithmetic) basis so as to produce, for example, a "bull's eye" image of the cardiac myocardium tissue as the final output image depicted in FIG. 11 on the right side.

Figure 12:
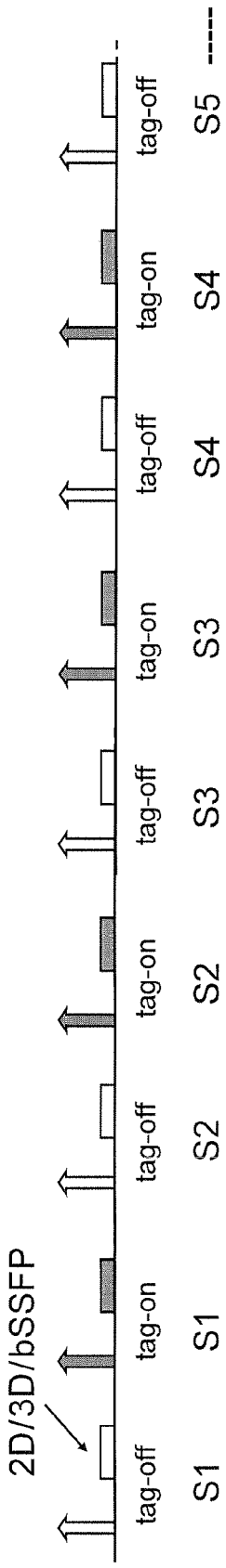
FIG. 12 is a schematic depiction of an alternating tag-on/tag-off data acquisition sequence in one breath-hold.

FIG. 12 schematically depicts in somewhat more detail the alternating interleaved tag-on/tag-off data acquisition sub-sequences to be employed within one breath-hold for either 2D data acquisition or 3D data acquisition of a multi-slice imaged volume of coronary myocardium tissue slices.

Figure 13:
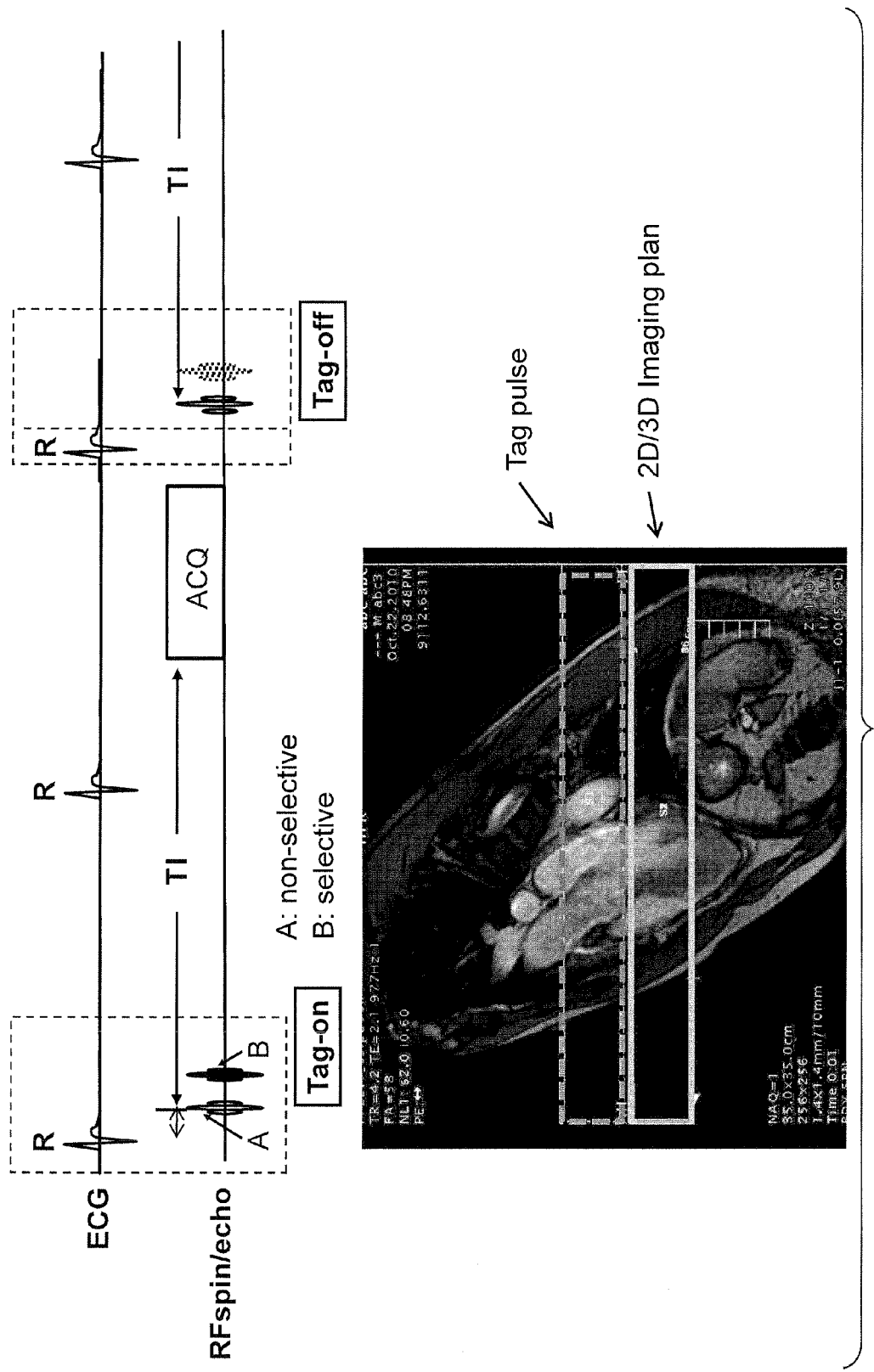
FIG. 13 is a schematic depiction of a 2D/3D imaging plan together with a schematic depiction of tag-on and tag-off sub-sequences synchronized with an ECG R-wave signal.

FIG. 13 depicts a somewhat more realistic locator/scout image with a superimposed tag pulse region (shown in dotted lines), as well as a proposed 2D/3D imaging volume (shown in solid lines). The first of a sequence of interleaved tag-on and tag-off data acquisition sub-sequences is also depicted as, in this case, coordinated with an ECG R-wave signal.

Figure 14:
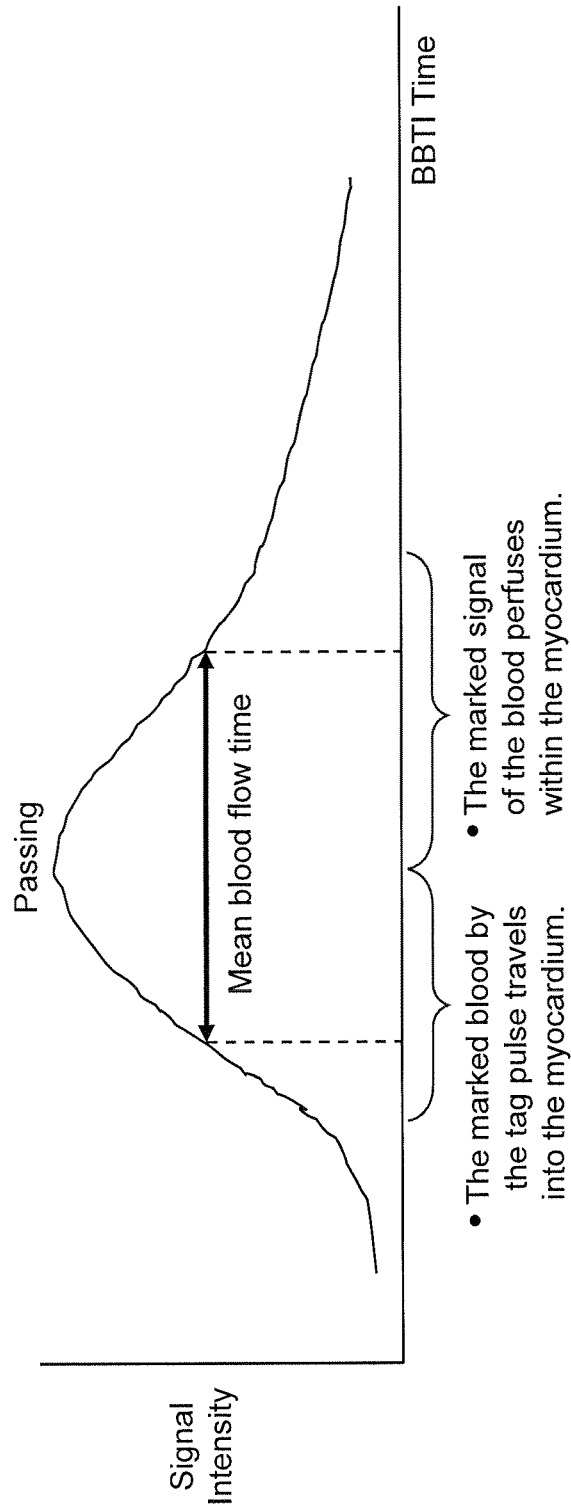
FIG. 14 is an exemplary plot of signal intensity versus varying BBTI times to facilitate calculation of mean blood flow time for perfusion into the myocardium.

FIG. 14 shows a plot of MRI signal intensity versus varied BBI times. This demonstrates, for example, a bolus of tagged blood entering the heart arteries and thus building up towards a maximum as it enters—followed by reduced signal as the blood perfuses within the myocardium. The mean blood flow time for blood perfusion into the myocardium can then be calculated from such a plot as schematically depicted in FIG. 14.

Figure 15A:
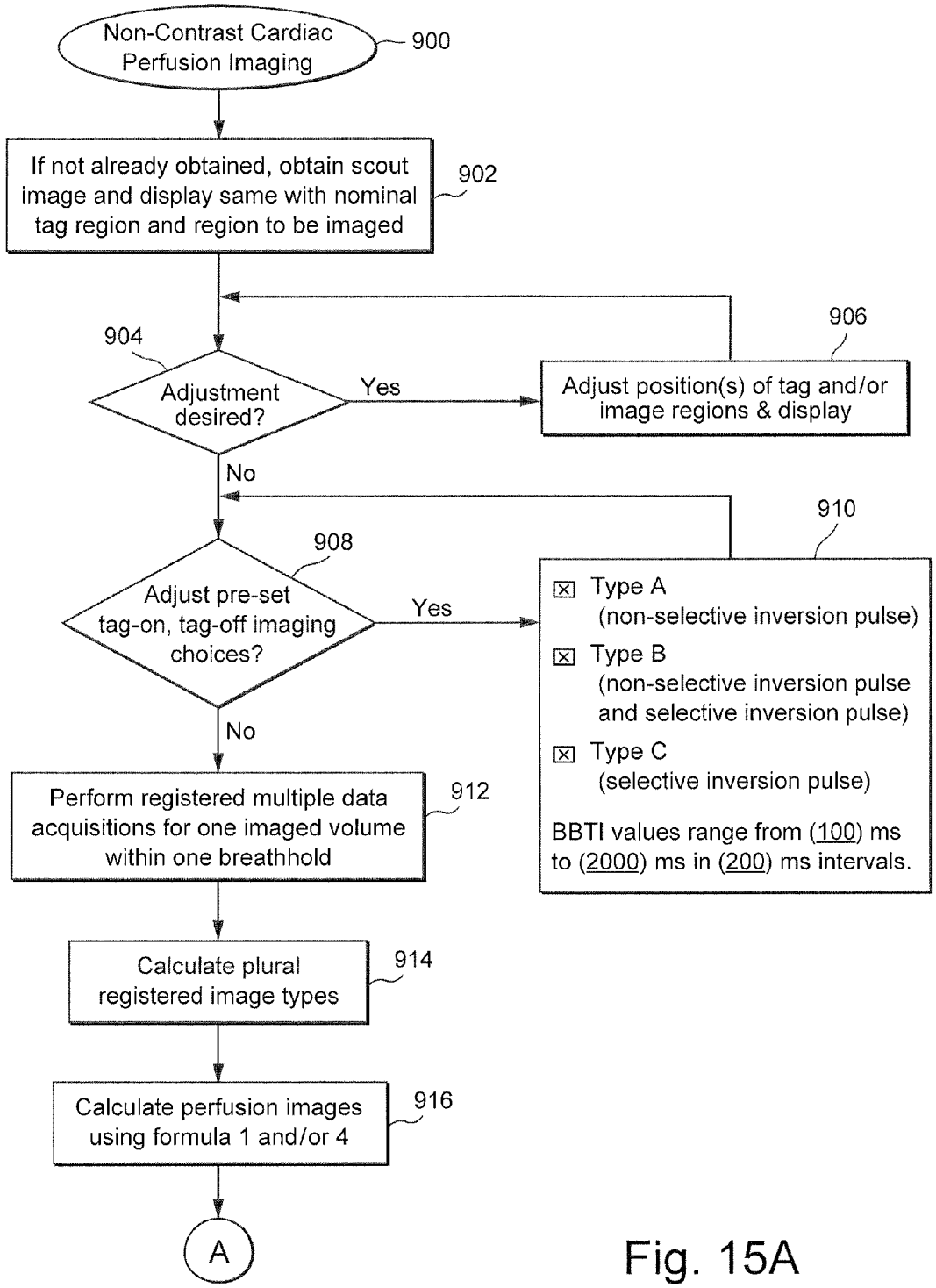
FIGS. 15A and 15B provide schematic illustrations of exemplary computer program code structures in the form of flow charts for implementing exemplary embodiments of Time-SLIP tag-on/tag-off 3D acquisition, image processing and display for non-contrast cardiac perfusion imaging.
Figure 15B:
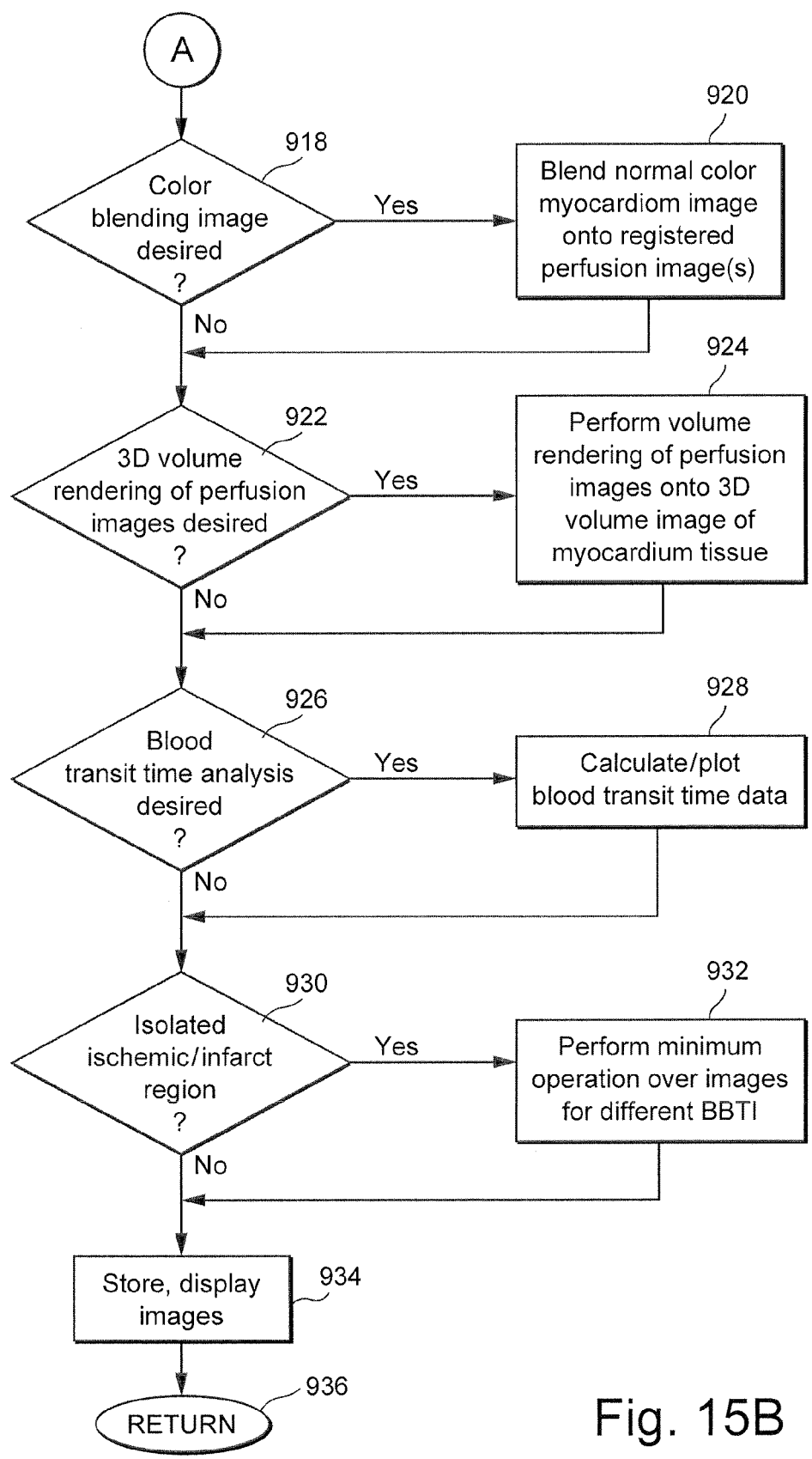

A schematic depiction of suitable computer program code structure for an exemplary embodiment is depicted at FIGS. 15A and 15B. Here, entry to a non-contrast cardiac perfusion imaging routine is made at 900 (e.g., from an over-arching operating system or other MRI system control software). At 902, if a locator/scout image of the desired cardiac tissue has not already been obtained and displayed, then such is obtained and displayed here, along with a nominal tag region and a region to be imaged (e.g., such as depicted in the lower part of FIG. 13).

At 904, the operator is given an opportunity to adjust placement of the tag region and image region. If adjustment desire is indicated, then at 906, the operator adjusts the positions of the tag and/or image regions, such adjusted positions are reflected in the display, and control is passed back to step 904 to see if any further adjustment is desired. If not, then control passes to step 908 where an opportunity is given to adjust preset tag-on, tag-off and related imaging choices. If the operator elects to adjust such preset values, then control passes to step 910 where the operator is permitted choice of the types of tag-on/tag-off sub-sequences to be employed and the range of BBTI values in a Time-SLIP embodiment. As will be noted below, other sub-routine control parameters might also be entered at this point rather than providing separate operator choices at subsequent point(s) in the process.

Once the preset tag-on/tag-off and other related imaging choices have been made, then control passes to step 912 where the preset multiple data acquisitions are performed within one breath-hold. In particular, this provides, in accordance with the earlier explained exemplary embodiment, registered multiple image data acquisitions for non-contrast tag-on and tag-off images to be further processed.

Once sufficient raw data has been acquired to fill k-space for at least one tag-on and at least one tag-off image volume, then the actual images are calculated and generated at step 914. At step 916, hybrid perfusion images are generated using predefined formulae such as Equation 1 and/or Equation 4 described above so as to differentially calculate a resultant image I.

At step 918, the operator is given a choice as to whether color blending of the resultant image I is desired. If so, then at step 920, a blending may be accomplished between (a) a normal monochrome myocardium image (e.g., type A) and (b) a registered color-valued processed perfusion image I. At step 922, the operator is given a choice as to whether 3D volume rendering of perfusion images is desired. If so, then at step 924, volume rendering of perfusion images is performed (e.g., onto a 3D image of myocardium ventricular tissue). At step 926, the operator is given an option for blood transit time analysis. If that option is selected, then at step 928, the blood transit time is calculated (e.g., possibly including a visualized and displayed plot of tagged blood signal intensity versus BBTI time as in FIG. 14).

At step 930, the operator is given a choice as to whether it is desired to generate a display that can isolate ischemic and/or infarct regions of the imaged myocardium. If so, then at step 932, a minimum operation is performed over perfusion images for different BBTI so as to result in an image that shows a "bright" region where there has been little change in signal intensity over a fairly large number of BBTI values.

At step 934, all or some of the generated images may be stored or displayed to the operator before a return is effected at 936 to the calling system.

While certain embodiments of the invention have been described, these embodiments have been presented by way of example only, and are not intended to limit the scope of the invention. Indeed, the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms or modifications as would fall within the scope and spirit of the invention.

What is claimed is:

1. A magnetic resonance imaging (MRI) system comprising:
    an MRI gantry including a static magnet, gradient magnet coils and at least one radio frequency (RF) coil defining a patient imaging volume into which a chest region of a patient is located; and
    RF receiver and transmitter circuits coupled to said at least one RF coil;
    control circuits connected to said gantry and to said RF receiver and transmitter circuits, said control circuits having an operator display and an operator control input port for configuring and operating said MRI system to acquire and process MRI data from said patient,
    said control circuits being configured
        (i) to acquire first, second and third MRI data sets for a same region within the chest region without use of a contrast-enhancing chemical agent by performing the following three data acquisition sub-sequences within one scan sequence, (A) using a non-selective inversion pulse without a selective inversion pulse, (B) using a non-selective inversion pulse and a selective inversion pulse, and (C) using a selective inversion pulse without a non-selective inversion pulse;
        (ii) to repeat the acquisition of said first, second and third MRI data sets for each of plural different black blood time to inversion (BBTI) values, wherein three data acquisition sub-sequences are performed respectively for a same BBTI value;
        (iii) image processing circuits configured to generate first, second and third images for the same region for each of plural different BBTI values based on the first, second and third MRI data sets and to generate a processed cardiac perfusion image by differentially combining respectively corresponding pixels of the first, second and third images; and
        (iv) an output circuit for outputting said processed cardiac perfusion image for digital storage or digital data transmission.

2. A magnetic resonance imaging (MRI) system comprising:
    an MRI gantry including a static magnet, gradient magnet coils and at least one radio frequency (RF) coil defining a patient imaging volume into which the chest region of a patient is located; and
    RF receiver and transmitter circuits coupled to said at least one RF coil;
    control circuits connected to said gantry and to said RF receiver and transmitter circuits, said control circuits having an operator display and an operator control input port for configuring and operating said MRI system to acquire and process MRI data from said patient,
    said control circuits being configured
        (i) to acquire MRI data sufficient to generate without use of a contrast-enhancing chemical agent (a) a first type image using a data acquisition sub-sequence including an IR (inversion recovery) pulse and (b) a second type image using a data acquisition sub-sequence including an IR pulse, the first type image being different from the second type image, and
        (ii) to repeat the acquisition of said MRI data for each of plural different black blood time to inversion (BBTI) values;
    image processing circuits configured to combine respectively corresponding complex-values of the first type image pixels and second type image pixels to produce a resultant cardiac perfusion image I in accordance with the following formula $$I_i = (\theta_o - \min(\theta_o, |A_i - B_i|))F(\max(|A_i|, |B_i|), T_{BBTI})$$

where:
$A_i$ and $B_i$ are complex number values of a pixel at pixel location I of a first type image and a second type image, respectively,
$\theta_o$ is a threshold value, and
F is a continuous threshold function of $|A_i|$ and $|B_i|$ and $T_{BBTI}$ black blood time to inversion (BBTI),
wherein:
said control circuits are further configured to acquire MRI data within one patient breath-hold sufficient to generate without use of a contrast-enhancing chemical agent (c) at least one tag-on third type cardiac perfusion image using a data acquisition sub-sequence including a spatially selective IR pulse, and
said image processing circuits are further configured to combine respectively corresponding complex-values of the first type image pixels and third type image pixels to produce a resultant cardiac perfusion image I in accordance with the following formula $$I_i = |A_i - B_i| F(|C_i - A_i|, T_{BBI})$$

where $A_i$, $B_i$ and $C_i$ are complex number values of a pixel at pixel location i of a first type image, a second type image and a third type image, respectively, and $T_{BBTI}$ is the black blood time to inversion (BBTI).

3. An MRI system as in claim 2, wherein said image processing circuits are configured to define the function F as a sigmoid function.

4. A magnetic resonance imaging (MRI) system, comprising:
    an MRI gantry including a static magnet, gradient magnet coils and at least one radio frequency (RF) coil defining a patient imaging volume into which the chest region of a patient is located;
    RF receiver and transmitter circuits coupled to said at least one RF coil;
    control circuits connected to said gantry and to said RF receiver and transmitter circuits, said control circuits having an operator display and an operator control input port for configuring and operating said MRI system to acquire and process MRI data from said patient,
    said control circuits being configured to acquire MRI data within one patient breath-hold sufficient to generate without use of a contrast-enhancing chemical agent (a) at least one tag-off first type cardiac perfusion image using a data acquisition sub-sequence including a non-selective IR (inversion recovery) pulse and (b) at least one tag-on second type cardiac perfusion image using a data acquisition sub-sequence including a non-selective IR pulse and a spatially selective IR pulse, and image processing circuits configured to generate processed cardiac perfusion image pixels by differentially combining respectively corresponding pixels of tag-on and tag-off images acquired for each BBTI value;

wherein said image processing circuits are configured to combine respectively corresponding complex-values of the first type and second type image pixels to produce a resultant cardiac perfusion image I in accordance with the following formula $$I_i = (\theta_o - \min(\theta_o, |A_i - B_i|)) F(\max(|A_i|, |B_i|), T_{BBTI})$$

where:

$A_i$ and $B_i$ are complex number values of a pixel at pixel location i of a first type image and a second type image, respectively, $\theta_o$ is a threshold value, and F is a continuous threshold function of $|A_i|$ and $|B_i|$ and $T_{BBTI}$ black blood time to inversion (BBTI);

wherein said image processing circuits are configured to define the function F as a sigmoid function, and wherein said sigmoid function F is defined as:

$$F(x, t) = \left( \frac{1}{1 + \exp\left(-\frac{x - g(t)}{6g(t)}\right)} \right)$$

where x represents pixel value and is a function that represents threshold changes depending on BBTI.

5. An MRI system as in claim 4, wherein g(t) is based at least in part on T1 recovery time.

6. An MRI system as in claim 5, wherein:

$$g(t) = C \max\left(\varepsilon, \left|1 - 2\exp\left(-\frac{t}{T_1}\right)\right|\right)$$

where C and $\varepsilon$ are user-adjustable parameters and $T_1$ is the T1 recovery constant of myocardium.

7. An MRI system as in claim 1, wherein tag-on and tag-off MRI data acquisition sub-sequences are interleaved with respect to time within an overall MRI data acquisition sequence within one patient breath-hold.

8. An MRI system as in claim 1, wherein said sub-sequences are 3D MRI data acquisition sequences encompassing a multi-slice patient volume.

9. An MRI system as in claim 1, wherein said sub-sequences comprise a plurality of 2D MRI data acquisition sequences encompassing a multi-slice patient volume.

10. An MRI system as in claim 1, further comprising:
image processing circuits configured to differentially combine respectively corresponding complex-values of the first and second images to produce a resultant image I which is then further combined by color-blending on a pixel by pixel basis with said first image, said resultant image I and said first image having pixels of different color values.

11. An MRI system as in claim 10, wherein said resultant image I is assigned color-valued pixel values while said first image is assigned monochrome pixel values.

12. An MRI system as in claim 1, wherein said MRI data acquisition sub-sequences are multi-slice data acquisitions using a range of black blood time to inversion (BBTI) values to generate a data set which images cardiac perfusion as a function of time that can be viewed in cine fashion or otherwise analyzed for perfusion dynamics, with BBTI as a time-dimension variable.

13. An MRI system as in claim 12, wherein the range of BBTI values is sufficient to plot or otherwise calculate a mean transit time for blood entering the coronary arteries until it later is dissipated in the myocardium.

14. An MRI system as in claim 1, wherein said MRI data acquisition sub-sequences are multi-slice data acquisitions using a range of black blood time to inversion (BBTI) values to generate a data set which images cardiac perfusion as a function of time, said MRI system further comprising:
image processing circuits configured to perform a pixel minimum value selection between a threshold value and actual pixel value of all acquired images over a range of BBTI values to produce a composite image isolating possible ischemic and/or infarct regions of cardiac myocardium as areas of distinguishable contrast where acquired MRI signals did not change significantly between the first and second images over many BBTI values.

15. A magnetic resonance imaging (MRI) method comprising:
using an MRI gantry including a static magnet, gradient magnet coils and at least one radio frequency (RF) coil defining a patient imaging volume into which the chest region of a patient is located, RF receiver and transmitter circuits coupled to said at least one RF coil
(i) to acquire MRI data sufficient to generate, within one patient breath-hold, without use of a contrast-enhancing chemical agent, (a) a first image using a data acquisition sub-sequence including an IR (inversion recovery) pulse, (b) a second image using a data acquisition sub-sequence including an IR pulse, and (c) a third type image using a data acquisition sub-sequence including a spatially selective IR pulse, the first, second and third type images being different from each other, wherein each of said first, second and third data acquisition sub-sequences is one of the following three types (A) using a non-selective inversion pulse without a selective inversion pulse, (B) using a non-selective inversion pulse and a selective inversion pulse, and (C) using a selective inversion pulse without a non-selective inversion pulse;
(ii) to repeat the acquisition of said MRI data for each of plural different black blood time to inversion (BBTI) values;
(iii) to generate first, second and third images for the same region for each of plural different BBTI values based on the acquired MRI data, and to generate a processed cardiac perfusion image, by differentially combining respectively corresponding pixels of the first, second and third images; and
(iv) to output said processed cardiac perfusion image for digital storage or digital data transmission.

16. An MRI method as in claim 15, further comprising:
using an image processor to combine respectively corresponding complex-values of the first image pixels and second image pixels to produce a resultant cardiac perfusion image I in accordance with the following formula $$I_i = \min(\theta_o, |A_i - B_i|)) F(\max(|A_i|, |B_i|), T_{BBTI})$$

where:

$A_i$ and $B_i$ are complex number values of a pixel at pixel location i of a first image and a second image, respectively, $\theta_o$ is a threshold value, and F is a continuous threshold function of $|A_i|$ and $|B_i|$ and $T_{BBTI}$ black blood time to inversion (BBTI).

17. A magnetic resonance imaging (MRI) method using an MRI gantry including a static magnet, gradient magnet coils and at least one radio frequency (RF) coil defining a patient imaging volume into which the chest region of a patient is located, RF receiver and transmitter circuits coupled to said at least one RF coil to acquire MRI data within one patient breath-hold sufficient to generate without use of a contrast-enhancing chemical agent (a) at least one tag-off first type cardiac perfusion image using a data acquisition sub-sequence including a non-selective IR (inversion recovery) pulse and (b) at least one tag-on second type cardiac perfusion image using a data acquisition sub-sequence including a non-selective IR pulse and a spatially selective IR pulse, and using at least one image processor to generate processed cardiac perfusion image pixels by differentially combining respectively corresponding pixels of tag-on and tag-off images acquired for each BBTI value;

wherein said image processor combines respectively corresponding complex-values of the first type image pixels and second type image pixels to produce a resultant cardiac perfusion image I in accordance with the following formula $$I_i = (\theta_o - \min(\theta_o, |A_i - B_i|)) F(\max(|A_i|, |B_i|), T_{BBTI})$$

where:

$A_i$ and $B_i$ are complex number values of a pixel at pixel location i of a first type image and a second type image, respectively, $\theta_o$ is a threshold value, and F is a continuous threshold function of $|A_i|$ and $|B_i|$ and $T_{BBTI}$ black blood time to inversion (BBTI), and wherein F is defined as:

$$F(x, t) = \left( \frac{1}{1 + \exp\left(-\frac{x - g(t)}{6g(t)}\right)} \right)$$

where x represents pixel value and g(t) is a function that represents threshold changes depending on BBTI.

18. An MRI method as in claim 17, wherein:

$$g(t) = C \max\left(\varepsilon, \left| 1 - 2 \exp\left(-\frac{t}{T_1}\right) \right|\right)$$

where C and $\varepsilon$ are parameters to be adjusted and $T_1$ is the T1 recovery constant of myocardium.

19. An MRI system as in claim 1, wherein:
said MRI data is acquired within one patient breath-hold.

20. An MRI system as in claim 1, wherein:
the first image is a tag-off image using a data acquisition sub-sequence including a non-selective IR pulse and the second image is a tag-on image using a data acquisition sub-sequence including a non-selective IR pulse and a spatially selective IR pulse.

21. An MRI system as in claim 1, wherein:
the first, second and third images are perfusion images.

22. An MRI system as in claim 1, further comprising:
image processing circuits configured to generate processed cardiac perfusion image pixels by differentially combining respectively corresponding pixels of two images acquired for each BBTI value.

* * * * *